(12) United States Patent
Yokhin et al.

(10) Patent No.: US 7,321,652 B2
(45) Date of Patent: Jan. 22, 2008

(54) MULTI-DETECTOR EDXRD

(75) Inventors: Boris Yokhin, Nazareth Illit (IL);
Alexander Krokhmal, Haifa (IL); Alex Tokar, Haifa (IL)

(73) Assignee: Jordan Valley Semiconductors Ltd., Migdal Ha'emek (IL)

( * ) Notice: Subject to any disclaimer, the term of this patent is extended or adjusted under 35 U.S.C. 154(b) by 0 days.

(21) Appl. No.: 11/532,162

(22) Filed: Sep. 15, 2006

(65) Prior Publication Data

US 2007/0058779 A1 Mar. 15, 2007

Related U.S. Application Data

(60) Provisional application No. 60/717,820, filed on Sep. 15, 2005.

(51) Int. Cl.
*G01T 1/36* (2006.01)
(52) U.S. Cl. .......................................... 378/82; 378/83
(58) Field of Classification Search ................ 378/90, 378/82–83, 70, 71, 88
See application file for complete search history.

(56) References Cited

U.S. PATENT DOCUMENTS

| 6,108,398 | A | 8/2000 | Mazor et al. |
| 6,118,850 | A | 9/2000 | Mayo et al. |
| 6,389,102 | B2 * | 5/2002 | Mazor et al. ................. 378/89 |
| 6,754,304 | B1 * | 6/2004 | Kumakhov ................. 378/45 |

OTHER PUBLICATIONS

U.S. Appl. No. 60/717,820.
V.R. Albertini, et al., "Energy-Dispersive X-Ray Diffraction on Thin Films and its Application To Superconducting Samples", J. Appl. Cryst. (2003). 36, 43-47.

* cited by examiner

*Primary Examiner*—Hoon Song
(74) *Attorney, Agent, or Firm*—Smith, Gambrell & Russell, LLP

(57) ABSTRACT

A method for analysis of a sample includes irradiating an area of the sample with a polychromatic X-ray beam. X-rays scattered from the sample are detected using a plurality of detectors simultaneously in different, respective positions, whereby the detectors generate respective outputs. Energy-dispersive processing is applied to the outputs of the detectors so as to identify one or more X-ray diffraction lines of the sample.

16 Claims, 4 Drawing Sheets

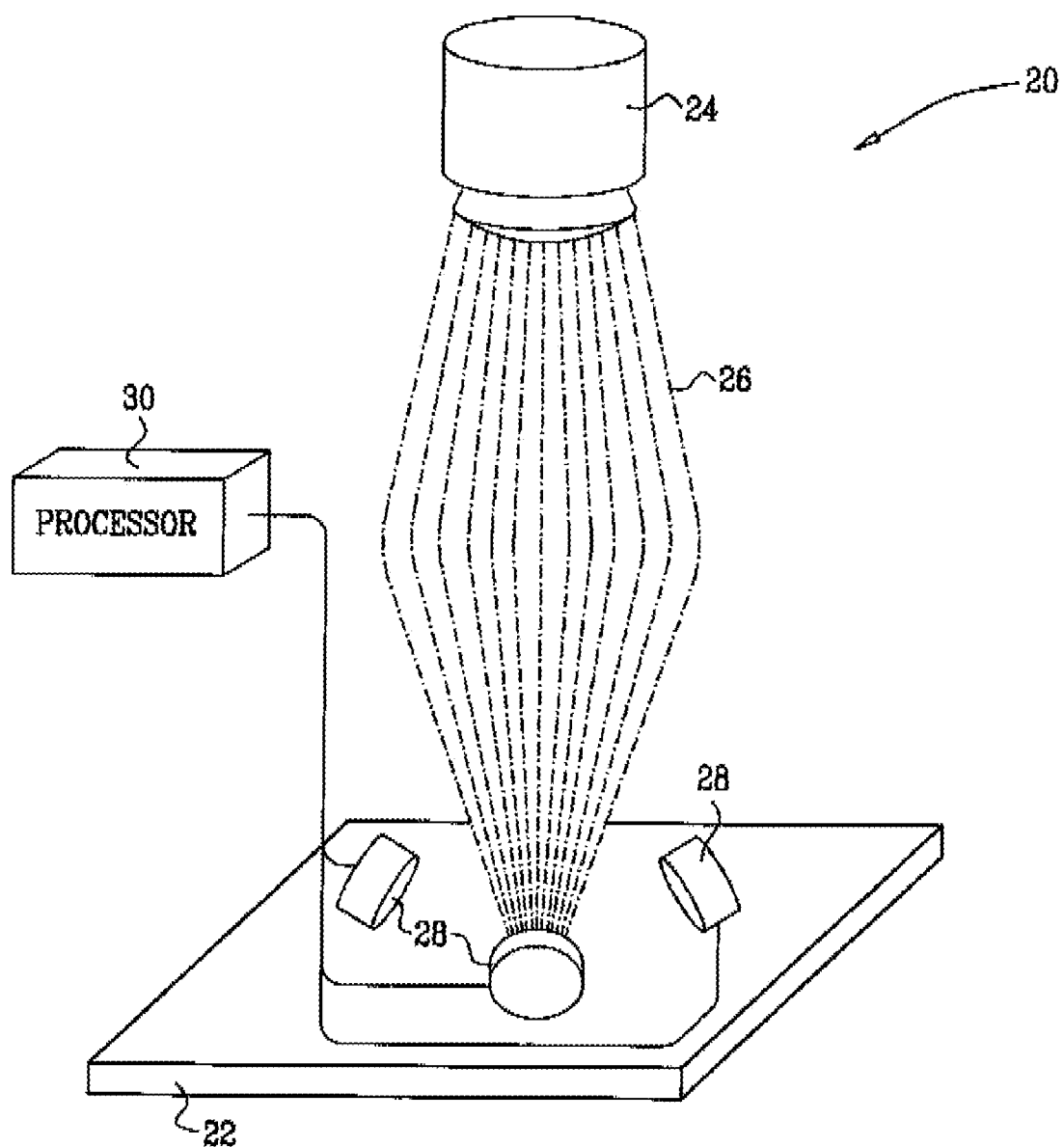

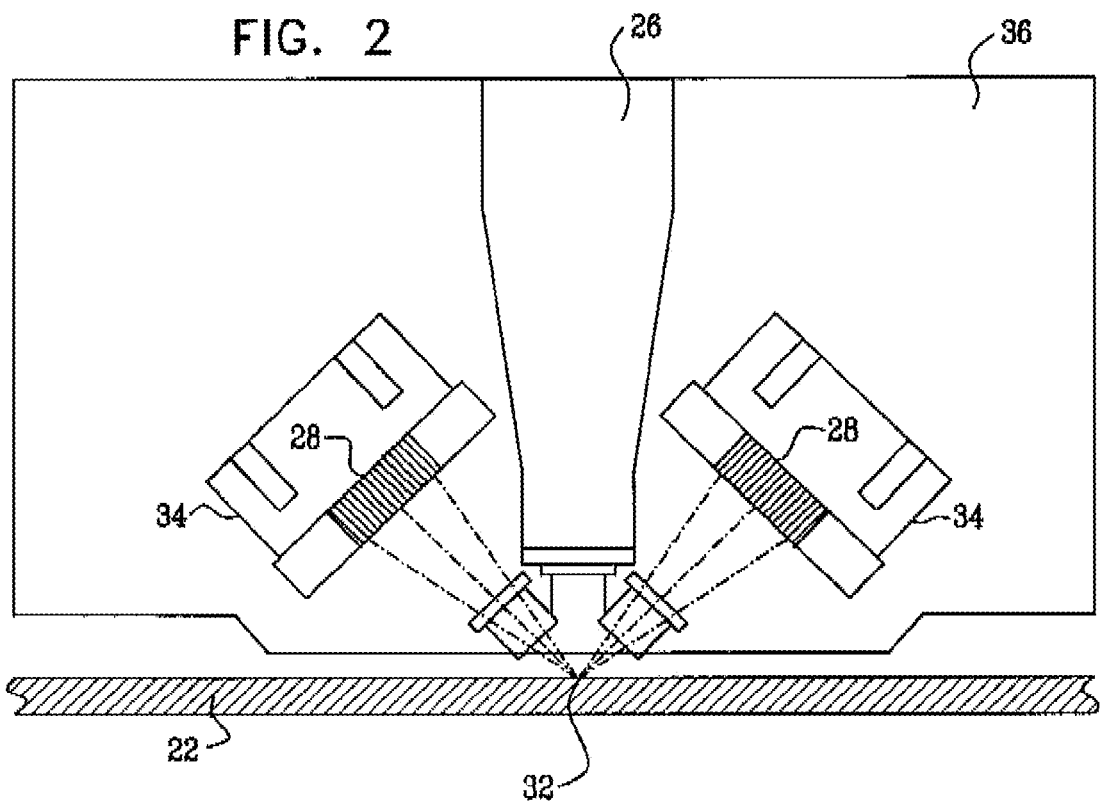
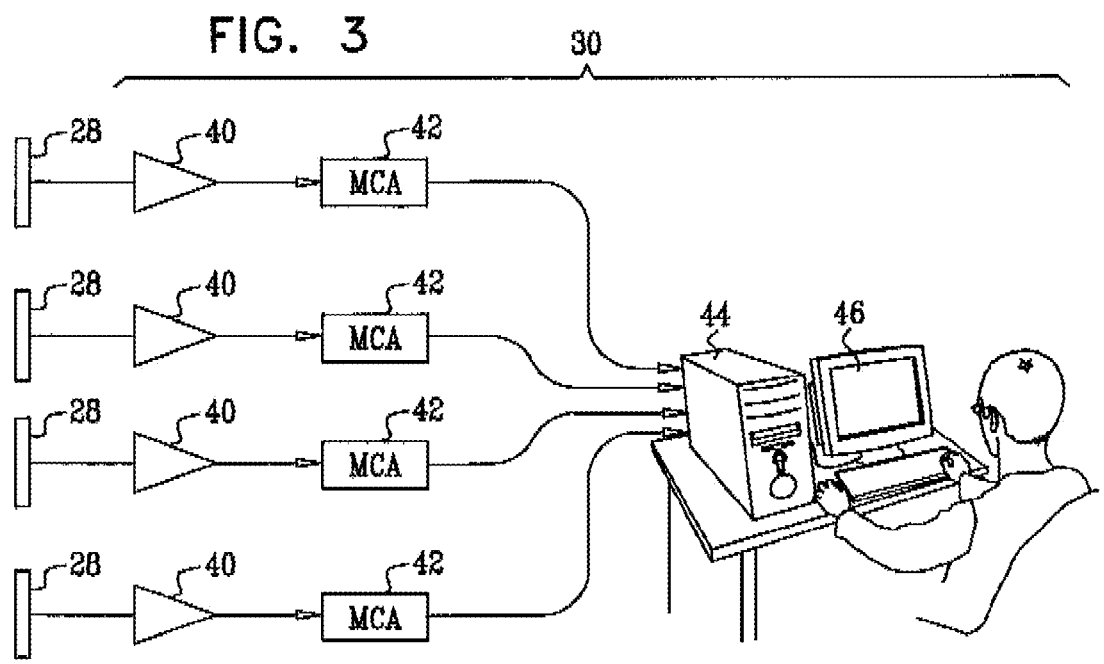

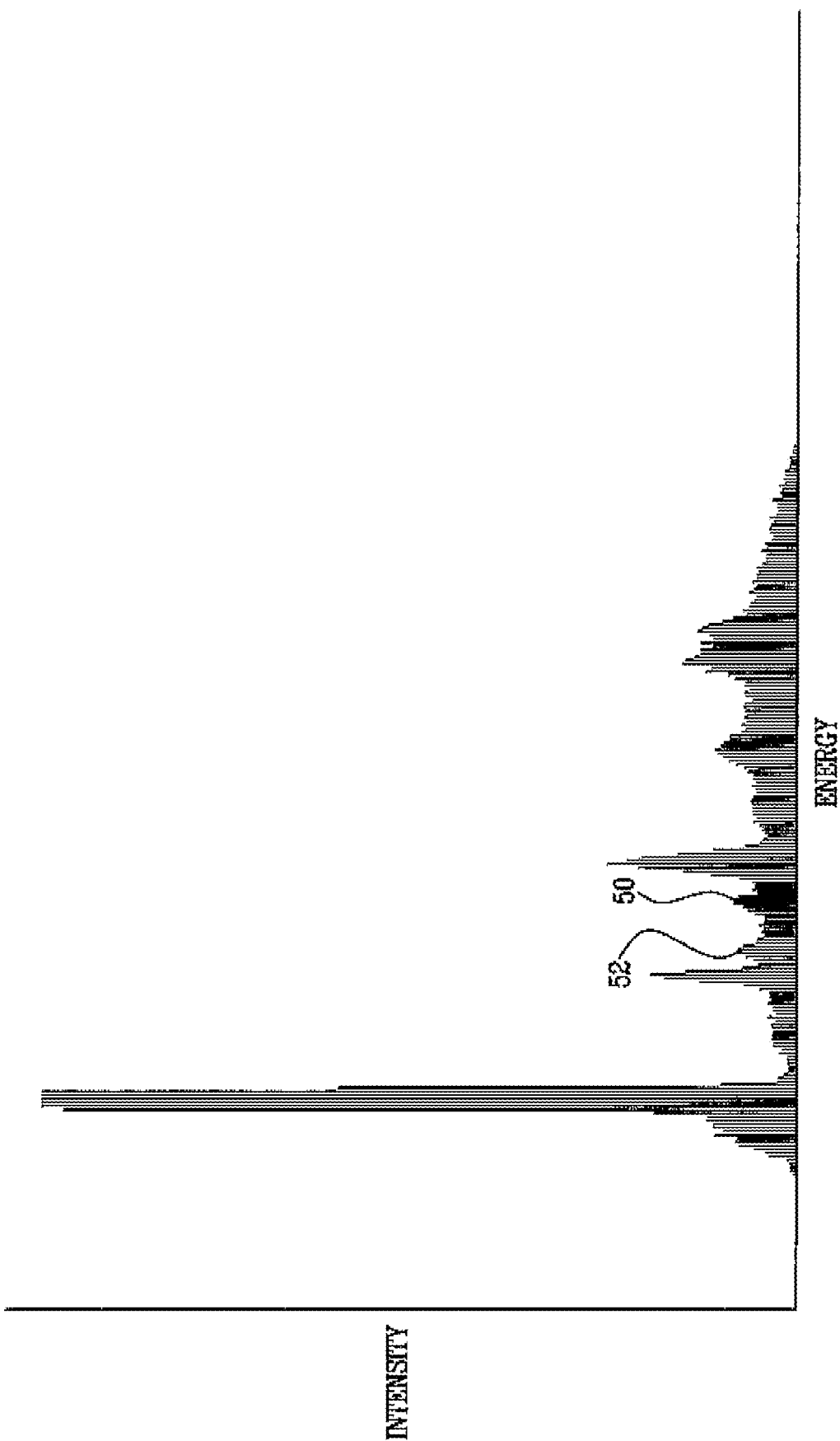

US 7,321,652 B2

MULTI-DETECTOR EDXRD

CROSS-REFERENCE TO RELATED APPLICATION

This application claims the benefit of U.S. Provisional Patent Application 60/717,820, filed Sep. 15, 2005, which is incorporated herein by reference.

FIELD OF THE INVENTION

The present invention relates generally to analytical instruments, and specifically to instruments for measuring X-ray diffraction.

BACKGROUND OF THE INVENTION

Energy-dispersive X-ray diffraction (EDXRD) is known in the art as a method for measuring properties of crystalline samples. An X-ray source generates a polychromatic X-ray beam, which is incident on a sample being examined. X-rays are diffracted from the sample over a range of angles with respect to the incident beam. An energy-dispersive X-ray detector is arranged to capture the diffracted X-ray beam at a certain angle. The detector is used to measure the diffracted beam intensity as a function of photon energy, and thus to provide a spectrum of the diffracted X-rays.

An exemplary EDXRD system is described in U.S. Pat. No. 6,118,850. EDXRD may be used, inter alia, for analyzing thin films, as described, for example, by Albertini et al., in "Energy-Dispersive X-Ray Diffraction on Thin Films and Its Application to Superconducting Samples," *Journal of Applied Crystallography* 36 (2003), pages 43-47. This article and the above-mentioned patent are incorporated herein by reference.

SUMMARY OF THE INVENTION

Existing systems for EDXRD suffer from a number of shortcomings, among them low throughput. Embodiments of the present invention provide improved systems for EDXRD using multiple detectors simultaneously, and thus give enhanced throughput and greater versatility relative to systems known in the art.

There is therefore provided, in accordance with an embodiment of the present invention, a method for analysis of a sample, including:

irradiating an area of the sample with a polychromatic X-ray beam;

detecting X-rays scattered from the sample using a plurality of detectors simultaneously in different, respective positions, whereby the detectors generate respective outputs; and applying energy-dispersive processing to the outputs of the detectors so as to identify one or more X-ray diffraction lines of the sample.

In disclosed embodiments, irradiating the area includes focusing the X-ray beam to irradiate a spot on the sample. The X-ray beam may be directed to impinge on a surface of the sample in a direction normal to the surface or at a non-normal angle relative to the surface, In some embodiments, detecting the X-rays includes arranging two or more of the detectors to detect the scattered X-rays at different azimuths and equal elevation angles relative to a surface of the sample. In this case, applying the energy-dispersive processing typically includes determining respective counts of X-ray photons incident on each of the two or more of the detectors at an X-ray energy corresponding to at least one of the X-ray diffraction lines, and summing the respective counts.

Alternatively, detecting the X-rays includes arranging two or more of the detectors to detect the scattered X-rays at different, respective elevation angles relative to a surface of the sample. In this case, applying the energy-dispersive processing may include determining respective counts of X-ray photons incident on each of the two or more of the detectors at respective X-ray energies for which the respective elevation angles correspond to Bragg angles of the sample.

There is also provided, in accordance with an embodiment of the present invention, apparatus for analysis of a sample, including:

an X-ray source, which is operative to irradiate an area of the sample with a polychromatic X-ray beam;

a plurality of detectors in different, respective positions, which are arranged to detect simultaneously X-rays scattered, from the sample and to generate respective outputs responsively to the detected X-rays; and a processor, which is adapted to apply energy-dispersive processing to the outputs of the detectors so as to identify one or more X-ray diffraction lines of the sample.

The present invention will be more fully understood from the following detailed description of the embodiments thereof, taken together with the drawings in which:

BRIEF DESCRIPTION OF THE DRAWINGS

FIG. 1 is a schematic, pictorial view of a system for EDXRD, in accordance with an embodiment of the present invention;

FIG. 2 is a schematic, sectional view of an irradiation and detection assembly for use in EDXRD, in accordance with an embodiment of the present invention;

FIG. 3 is a block diagram that schematically illustrates a signal processor for EDXRD, in accordance with an embodiment of the present invention;

FIG. 4 is a schematic plot of an exemplary EDXRD spectrum, acquired in accordance with an embodiment of the present invention.

DETAILED DESCRIPTION OF EMBODIMENTS

Figure 5:
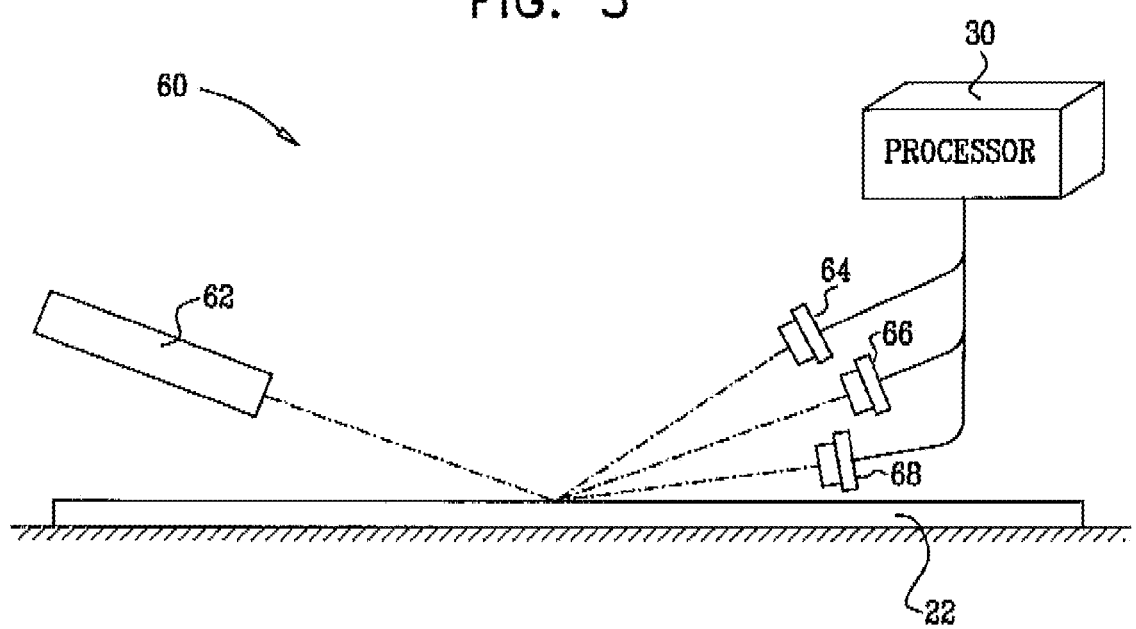
FIG. 5 is a schematic side view of a system for EDXRDL, in accordance with another embodiment of the present invention.

FIG. 1 is a schematic, pictorial view of a system 20 for EDXRD, in accordance with an embodiment of the present invention. In the pictured embodiment, the system is used for measurement and analysis for X-ray scattering from a thin film on the surface of a semiconductor wafer 22, but the system may likewise be applied to samples of other types. A polychromatic X-ray source 24, typically an X-ray tube, emits a beam of X-rays, which is focused to irradiate a small spot on the surface of the sample. In the present embodiment, the X-rays are focused by a monolithic polycapillary optic 26, such as those produced by X-Ray Optical Systems, Inc., of Albany, N.Y. Alternatively, other types of focusing optics may also be used, such as a monocapillary optic, a curved reflector, or pinhole optics, as are known in the art.

X-rays scattered from the surface of wafer 22 are captured by multiple detectors 28, which are arrayed around the polycapillary optic. A similar sort of arrangement, using multiple detectors for measurement of X-ray fluorescence, is described in U.S. Pat. No. 6,108,398, whose disclosure is incorporated herein by reference. Although three detectors are shown in FIG. 1, spaced roughly 90° apart (with a fourth detector hidden behind optic 26), a larger or smaller number of detectors may alternatively be used. Detectors 28 may comprise, for example, silicon PIN diodes, such as X-ray detection diodes produced by Hamamatsu Photonics, K.K., of Hamamatsu City, Japan. These detectors output electrical pulses in response to incident X-ray photons, wherein the amplitude of each pulse is typically proportional to the energy of the incident photon. Alternatively, any other suitable type of energy-resolving X-ray detectors may be used. The signals output by detectors 28 are processed by a signal processor 30 in order to extract the EDXRD spectrum, as described further hereinbelow.

FIG. 2 is a schematic, sectional view of an irradiation and detection assembly 36 that may be used in system 20, in accordance with an of the present invention. In this view, two of the detectors 28, in respective detector housings 34, are shown on opposite sides of polycapillary optic 26. The optic focuses x-rays from source 24 onto a focal sport 32 on wafer 22. Detectors 28 are aimed to collect X-rays that are scattered from the irradiated spot over respective narrow angular ranges. In this example, the detection angles of the detectors are both at about 45° elevation, and they are separated in azimuth by 180°. The other two detectors (not shown in this figure) are typically arranged at the same elevation and are offset in azimuth by 90° relative to the detectors shown in FIG. 2, as noted above.

This angular arrangement of the detectors is shown only by way of example, and other arrangements may also be used. For instance, larger or smaller numbers of detectors may be deployed around the irradiated spot, with smaller or larger azimuthal separation between the detector. Moreover, the elevation angles of the detectors may be higher or lower than 45°. Furthermore, the elevation angles and/or azimuthal positions of the detectors may be adjustable in order to optimize the detector positions for the type of sample and diffraction peaks that are to be detected. Additionally or alternatively, different detectors may be placed at different elevation angles, so that EDXRD measurements may be made at multiple elevations simultaneously.

As yet another alternative, the polycapillary or other focusing optic may be arranged so that the x-ray beam is incident on the surface at an angle, such as 45°, rather than at normal incidence as shown in the figures to the wafer. This sort of arrangement is shown below in FIG. 5.

FIG. 3 is a block diagram that schematically illustrates elements of signal processor 30, in accordance with an embodiment of the present invention. The output of each detector 28 is amplified by a pulse amplifier 40, and the amplified pulses are input to an energy-dispersive processor, such as a digital multi-channel analyzer (MCA) 42. The MCA analyzes each pulse that is produced by the corresponding detector (resulting from incidence of an X-ray photon on the detector) in order to determine the energy of the corresponding photon. A similar sort of energy-dispersive signal processing arrangement is described, for example, in U.S. Pat. No. 6,389,102, whose disclosure is incorporated herein by reference.

A computer 44 counts the pulses that are detected by each MCA as a function of the corresponding photon energy, and thus generates an EDXRD spectrum. The spectrum may be shown in the form of a histogram over a range of energies, for example, on an output device, such as a display 46. Alternatively, the computer may determine and output the diffraction intensity at only one or a few energies of interest. If all the detectors are oriented at the same elevation angle relative to wafer 22, and azimuthal variations of intensity are not significant (as in polycrystalline samples), then the computer may simply sum the counts output by all of the detectors at each energy of interest in order to get a combined count with enhanced signal/noise ratio. Alternatively, the computer may monitor the outputs of the different detectors separately in order to obtain an output spectrum that is resolved not only by energy, but also by detector angle.

FIG. 4 is a schematic plot of an exemplary EDXRD spectrum acquired using system 20, in accordance with an embodiment of the present invention. The plot shows X-ray scattering as a function of energy from a thin copper film on a silicon wafer. The sample was irradiated by an X-ray tube (source 24) with anode voltage 8 kV and current 2 mA. Scattered X-rays were collected by detectors 28 at a 45° elevation angle. The spectrum in the figure shows the relative count of X-ray photons as a function of energy over the range up to about 8 keV, The copper film on the wafer was polycrystalline, and thus had different grains at different orientations. The 45° detection angle is equal to the Bragg angle for photons at about 3.2 keV diffracted from the 111 crystal plane and for photons at about 3.7 keV diffracted from the 200 crystal plane. Both of these energy peaks are seen in FIG. 3: a peak 50 at 3.7 keV and a peak 52 at 3.2 keV (although peak 52 overlaps with the argon Xb fluorescence line due to ambient argon in the test chamber). By way of example, the intensity of peak 50 summed over the four detectors was 50 counts/sec.

FIGS. 5 is a schematic side view of a system 60 for EDXRD, in accordance with another embodiment of the present invention. In this embodiment, an X-ray source 62 directs a polychromatic X-ray beam at a non-normal angle toward a point on wafer 22. Scattered X-rays are captured by detectors 64, 66, 68. Each of the detectors is positioned at a different angle relative to the axis of the irradiating beam. For example, each detector may be individually angled so as to capture a different, respective diffraction peak (or peaks) of interest at a convenient energy, depending on the type of material in the sample under study. This latter embodiment permits the positions and angles of the focusing optics and the detectors to be selected for maximal detection efficiency and throughput, while reducing overlap of the diffraction peaks with other spectral features, such as X-ray fluorescence lines, that may mask the diffraction peaks in the output spectrum.

Although certain specific configurations of X-ray sources and detectors are shown and described above, the principles of the present invention may similarly be applied in other system configurations. Furthermore, although the embodiments described above relate to X-ray diffraction, the techniques of the present invention may be extended to other energy ranges, as well. It will thus be appreciated that the embodiments described above are cited by way of example, and that the present invention is not limited to what has been particularly shown and described hereinabove. Rather, the scope of the present invention includes both combinations and subcombination of the various features described hereinabove, as well as variations and modifications thereof which would occur to persons skilled in the art upon reading the foregoing description and which are not disclosed in the prior art.

The invention claimed is:

1. A method for analysis of a sample, comprising:
   irradiating an area of the sample with a polychromatic X-ray beam;
   detecting X-rays scattered from the sample using a plurality of detectors simultaneously in different, respective positions, whereby the detectors generate respective outputs;
   applying energy-dispersive processing to the outputs of the detectors so as to identify one or more X-ray diffraction lines of the sample; and
   using the one or more X-ray diffraction lines to determine a crystalline structure of the sample.

2. The method according to claim 1, wherein irradiating the area comprises focusing the X-ray beam to irradiate a spot on the sample.

3. The method according to claim 1, wherein irradiating the area comprises directing the X-ray beam to impinge on a surface of the sample in a direction normal to the surface.

4. The method according to claim 1, wherein irradiating the area comprises directing the X-ray beam to impinge on a surface of the sample at a non-normal angle relative to the surface.

5. The method according to claim 1, wherein detecting the X-rays comprises arranging two or more of the detectors to detect the scattered X-rays at different azimuths and equal elevation angles relative to a surface of the sample.

6. The method according to claim 5, wherein applying the energy-dispersive processing comprises determining respective counts of X-ray photons incident on each of the two or more of the detectors at an X-ray energy corresponding to at least one of the X-ray diffraction lines, and summing the respective counts.

7. The method according to claim 1, wherein detecting the X-rays comprises arranging two or more of the detectors to detect the scattered X-rays at different, respective elevation angles relative to a surface of the sample.

8. The method according to claim 7, wherein applying the energy-dispersive processing comprises determining respective counts of X-ray photons incident on each of the two or more of the detectors at respective X-ray energies for which the respective elevation angles correspond to Bragg angles of the sample.

9. Apparatus for analysis of a sample, comprising:
   an X-ray source, which is operative to irradiate an area of the sample with a polychromatic X-ray beam;
   a plurality of detectors in different, respective positions, which are arranged to detect simultaneously X-rays scattered from the sample and to generate respective outputs responsively to the detected X-rays; and
   a processor, which is adapted to apply energy-dispersive processing to the outputs of the detectors so as to identify one or more X-ray diffraction lines of the sample.

10. The apparatus according to claim 9, wherein the X-ray source comprises optics for focusing the X-ray beam to irradiate a spot on the sample.

11. The apparatus according to claim 9, wherein the X-ray source is configured to direct the X-ray beam to impinge on a surface of the sample in a direction normal to the surface.

12. The apparatus according to claim 9, wherein the X-ray source is configured to direct the X-ray beam to impinge on a surface of the sample at a non-normal angle relative to the surface.

13. The apparatus according to claim 9, wherein two or more of the detectors are arranged to detect the scattered X-rays at different azimuths and equal elevation angles relative to a surface of the sample.

14. The apparatus according to claim 13, wherein the processor is arranged to determine respective counts of X-ray photons incident on each of the two or more of the detectors at an X-ray energy corresponding to at least one of the X-ray diffraction lines, and to sum the respective counts.

15. The apparatus according to claim 9, wherein two or more of the detectors are arranged to detect the scattered X-rays at different, respective elevation angles relative to a surface of the sample.

16. The apparatus according to claim 15, the processor is arranged to determine respective counts of X-ray photons incident on each of the two or more of the detectors at respective X-ray energies for which the respective elevation angles correspond to Bragg angles of the sample.

* * * * *